(12) United States Patent (10) Patent No.: US 10,874,999 B2
Ahn et al. (45) Date of Patent: Dec. 29, 2020

(54) MIXING DEVICE FOR CELL PRINTING COMPOSITION

(71) Applicants: T&R BIOFAB CO., LTD., Siheung-si (KR); Korea Polytechnic University Industry Academic Cooperation Foundation, Siheung-si (KR)

(72) Inventors: Geunseon Ahn, Siheung-si (KR); Jinhyung Shim, Siheung-si (KR); Jeongseok Lee, Siheung-si (KR); Ingyu Lee, Siheung-si (KR); Kyunghyun Min, Siheung-si (KR); Songwan Jin, Siheung-si (KR); Wonsoo Yun, Siheun-si (KR)

(73) Assignees: T&R BIOFAB CO., LTD., Siheung-si (KR); Korea Polytechnic University Industry Academic Cooperation Foundation, Siheung-si (KR)

( * ) Notice: Subject to any disclaimer, the term of this patent is extended or adjusted under 35 U.S.C. 154(b) by 0 days.

(21) Appl. No.: 16/450,113

(22) Filed: Jun. 24, 2019

(65) Prior Publication Data

US 2019/0314778 A1 Oct. 17, 2019

Related U.S. Application Data

(63) Continuation of application No. PCT/KR2017/014829, filed on Dec. 15, 2017.

(30) Foreign Application Priority Data

Dec. 23, 2016 (KR) .......................... 10-2016-0177709

(51) Int. Cl.
*B01F 15/02* (2006.01)
*B01F 7/18* (2006.01)
(Continued)

(52) U.S. Cl.
CPC ............ *B01F 15/0237* (2013.01); *B01F 7/18* (2013.01); *B01F 7/24* (2013.01);
(Continued)

(58) Field of Classification Search
CPC .......... B01F 15/00487; B01F 15/00824; B01F 15/0237; B01F 2015/00623;
(Continued)

(56) References Cited

U.S. PATENT DOCUMENTS 3,570,719 A * 3/1971 Schiff ............... B05C 17/00506
222/137
4,934,827 A * 6/1990 Taschke ............ B05C 17/00553
366/162.3
(Continued)

FOREIGN PATENT DOCUMENTS

CN 201380637 Y 1/2010
JP 2004313859 A 11/2004
(Continued)

OTHER PUBLICATIONS

"Happy Printing!", Application Note, CELLINK AB, Sweden, Jul. 2017, 2 pages.

*Primary Examiner* — Tony G Soohoo
(74) *Attorney, Agent, or Firm* — Nelson Mullins Riley & Scarborough LLP; Kongsik Kim

(57) ABSTRACT

The mixing device of cell printing composition according to the present disclosure comprises a first syringe comprising a first container for containing first liquid, a first moving element discharging the first liquid contained in the first container; a second syringe comprising a second container for containing second liquid, a second moving element discharging the second liquid contained in the second container; a mixing container which comprises a rotating mixing unit and receives the discharged first liquid and the
(Continued)

discharged second liquids; a power transmission unit for driving the first moving element, the second moving element and the mixing unit; a first threaded guide where the first moving element is movably connected; a second threaded guide where the second moving element is movably connected; and a rod for rotating the mixing unit.

5 Claims, 5 Drawing Sheets

(51) Int. Cl.
| | |
|---|---|
| *B01F 7/24* | (2006.01) |
| *B01F 15/00* | (2006.01) |
| *C12M 1/06* | (2006.01) |
| *B05C 17/005* | (2006.01) |
| *B33Y 40/00* | (2020.01) |
| *B05C 17/01* | (2006.01) |
| *B33Y 30/00* | (2015.01) |
| *C12M 1/26* | (2006.01) |

(52) U.S. Cl.
CPC .. *B01F 15/00487* (2013.01); *B05C 17/00566* (2013.01); *C12M 27/02* (2013.01); *B01F 2015/00623* (2013.01); *B01F 2215/0073* (2013.01); *B05C 17/0133* (2013.01); *B33Y 30/00* (2014.12); *B33Y 40/00* (2014.12); *C12M 33/00* (2013.01)

(58) Field of Classification Search
CPC .. B01F 2215/0073; B01F 3/0853; B01F 7/18; B01F 7/24
See application file for complete search history.

(56) References Cited

U.S. PATENT DOCUMENTS

| | | | | | |
|---|---|---|---|---|---|
| 4,986,443 | A | * | 1/1991 | Saur | B05C 17/00553 222/1 |
| 5,286,105 | A | * | 2/1994 | Herold | B05C 17/00516 222/137 |
| 5,860,739 | A | * | 1/1999 | Cannon | B05C 17/00553 222/137 |
| 6,457,609 | B1 | * | 10/2002 | Keller | B05C 17/00509 222/137 |
| 6,523,992 | B1 | * | 2/2003 | Bublewitz | A61C 9/0026 222/145.6 |
| 6,837,612 | B2 | * | 1/2005 | Bublewitz | A61C 9/0026 222/145.6 |
| 6,854,621 | B2 | * | 2/2005 | Keller | B05C 17/00509 222/137 |
| 6,932,237 | B2 | * | 8/2005 | Heymann | A61C 9/0026 222/1 |
| 6,932,243 | B2 | * | 8/2005 | Keller | B01F 13/002 222/145.6 |
| 7,972,057 | B2 | * | 7/2011 | Meyer | A61C 9/0026 222/325 |
| 8,147,122 | B2 | * | 4/2012 | Pieroni | B01F 7/008 222/145.6 |
| 9,415,408 | B2 | * | 8/2016 | Schultheiss | B05B 7/24 |
| 9,486,298 | B2 | * | 11/2016 | Peuker | B05C 17/00553 |
| 10,098,683 | B2 | * | 10/2018 | Vogt | A61B 17/8833 |
| 10,258,946 | B2 | * | 4/2019 | Buck | B05C 17/0103 |
| 10,293,362 | B2 | * | 5/2019 | Beckett | B05C 17/00566 |
| 2004/0108334 | A1 | * | 6/2004 | Strecker | G01F 11/029 222/145.1 |
| 2009/0263849 | A1 | | 10/2009 | Sun et al. | |
| 2010/0252574 | A1 | * | 10/2010 | Busin | A61C 5/64 222/137 |
| 2014/0036616 | A1 | * | 2/2014 | Ghosh | B05C 17/00566 366/129 |
| 2016/0016195 | A1 | * | 1/2016 | Beckett | B05C 17/00566 222/145.6 |
| 2019/0314778 | A1 | * | 10/2019 | Ahn | B01F 3/0853 |

FOREIGN PATENT DOCUMENTS

| | | |
|---|---|---|
| JP | 2016-526910 A | 9/2016 |
| KR | 10-0766619 B1 | 10/2007 |
| KR | 10-1362293 B1 | 2/2014 |
| KR | 10-1451794 B1 | 10/2014 |
| KR | 10-2015-0136892 A | 12/2015 |
| WO | 2015/066705 A1 | 5/2015 |

* cited by examiner

MIXING DEVICE FOR CELL PRINTING COMPOSITION

CROSS-REFERENCE TO RELATED APPLICATION

This application is a continuation of International Application No. PCT/KR2017/014829 filed on Dec. 15, 2017, which claims priority to Korean Application No. 10-2016-0177709 filed on Dec. 23, 2016. The applications are expressly incorporated herein by reference.

TECHNICAL FIELD

The present disclosure relates to a mixing device of cell printing composition, more specifically, to the device where injection and mixing of material are simultaneously carried out.

BACKGROUND

There have been a lot of studies for fabricating tissue structures by 3D printing technique. The technique is referred to as "cell printing" that cell printing composition of hydrogel such as collagen, gelatin, alginate and the like which contain cells, is discharged from a nozzle of a 3D bio-printer. The cell printing composition can be referred to as "bio-ink."

In order to make a cell printing composition, it is necessary to mix cell culture fluid and hydrogel which has sufficient viscosity for printing. CELLINK, a company based in Gothenburg, Sweden has sold such a mixing device, the trademark of which is "CELLMIXER." The mixing device has a mixing screw which operates in static state.

SUMMARY

The object of the present disclosure is to provide a mixing device of cell composition where material is dynamically mixed, and the injection and mixing of material is simultaneously carried out.

The mixing device of cell printing composition according to the present disclosure comprises a first syringe comprising a first container for containing first liquid, a first moving element discharging the first liquid contained in the first container; a second syringe comprising a second container for containing second liquid, a second moving element discharging the second liquid contained in the second container; a mixing container which comprises a rotating mixing unit and receives the discharged first liquid and the discharged second liquid; a power transmission unit for driving the first moving element, the second moving element and the mixing unit; a first threaded guide where the first moving element is movably connected; a second threaded guide where the second moving element is movably connected; and a rod for rotating the mixing unit.

The first moving element can move by the rotation of the first threaded guide; the second moving element can move by the rotation of the second threaded guide; and the first threaded guide, the second threaded guide, and the rod can be rotated by the power transmission unit.

The power transmission unit can comprise a ring gear, a sun gear which is rotated by the rotation of the ring gear, a first planetary gear which engages with the sun gear, and a second planetary gear which engages with the sun gear.

The first threaded guide can be rotated by the first planetary gear; the second threaded guide can be rotated by the second planetary gear; and the rod can be rotated by the sun gear.

The first moving element can be connected to the first threaded guide via a first connecting portion which is guided by the first threaded guide; and the second moving element can be connected to the second threaded guide via a second connecting portion which is guided by the second threaded guide.

The mixing device of the present disclosure can further comprise a first guard portion which has a first slot where the first connecting portion is guided; and a second guard portion which has a second slot where the second connecting portion is guided.

The mixing unit can comprise a second mixing portion which includes a spiral portion extending up and down direction.

The second mixing portion can further comprise a shaft extending up and down direction and the spiral portion can extend in the longitudinal direction of the shaft. The shaft can be connected to the rod and can be rotated by the rotation of the rod.

The first moving element can slide within the first container and the second moving element can slide within the second container.

The first connecting portion can comprise a first groove where the first guard is fit and the second connecting portion can comprise a second groove where the second guard is fit.

Any one of the first liquid and the second liquid can be cell culture fluid and the other can be hydrogel having a sufficient viscosity for cell printing.

According to the present disclosure, rotating a ring gear (40) of a power transmission unit (40) supplies a first liquid and a second liquid to a mixing container and simultaneously drives the mixing unit of the mixing container, thereby dynamically mixing the liquids.

DETAILED DESCRIPTION

Hereinafter, the present disclosure will be described in detail with reference to the accompanying drawings.

As those skilled in the art would realize, the described embodiments may be modified in various different ways, all without departing from the spirit or scope of the present disclosure.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Although the specification exemplarily explains a mixing device for two materials, it should be understood that a mixing device for more than two materials can be conceived without departing from the scope and the spirit of the present disclosure. In the present specification, the term "connected" means "connected via another component" as well as "directly connected."

Figure 1:
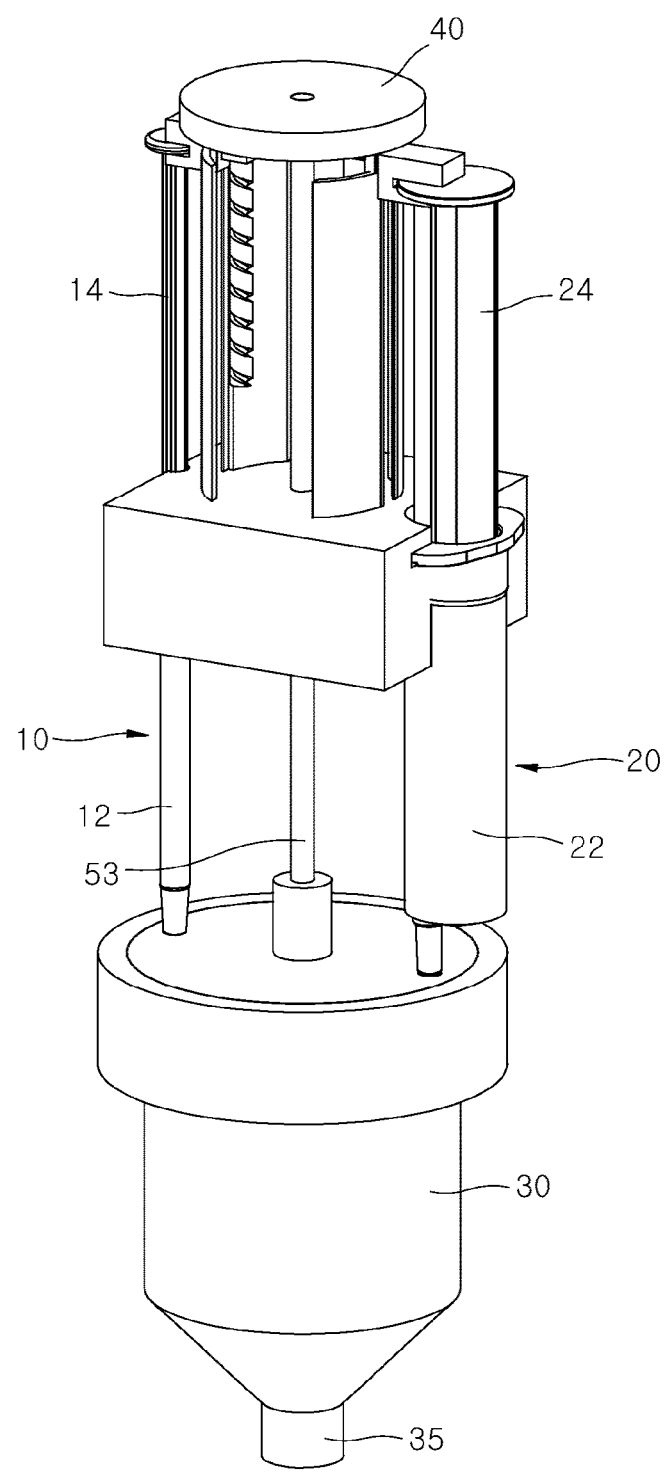
FIG. 1 is a perspective view of the mixing device of cell composition according to the present disclosure.
Figure 2:
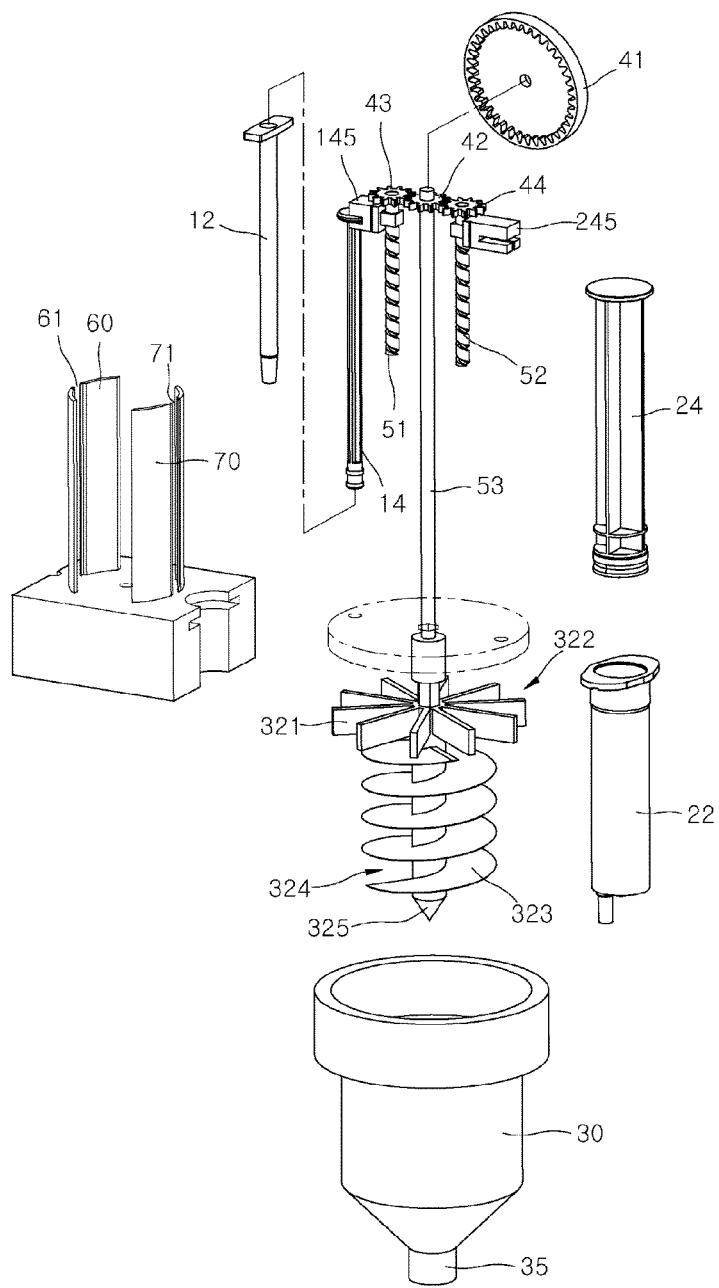
FIG. 2 is an exploded view of the device shown in FIG. 1

As shown in FIGS. 1 and 2, the mixing device of the present disclosure comprises a first syringe (10), a second syringe (20), a mixing container (30) and a power transmission unit (40).

The first syringe (10) comprises a first container (12) for containing a first liquid, and a first moving element (14) which discharges the first liquid contained in the first container (12) into the mixing container (30). The first moving element (14) can slide within the first container (12).

The first moving element (14) is movably connected to a first threaded guide (51) such that the element can move with respect to the first container (12) by rotation of the first threaded guide (51). The first moving element (14) is connected to the first threaded guide (51) via a first connecting element (145) which is guided by the first threaded guide (51). The first connecting element (145) has a first groove (146) formed therein. A first guard portion (60) is fit into the first groove (146) so that the first connecting element (145) is guided along a first slot (61) of the first guard portion (60).

The second syringe (20) comprises a second container (22) for containing a second liquid and a second moving element (24) for discharging the second liquid contained in the second container (22) into the mixing container (30). The second moving element (24) can slide within the second container (22).

The second moving element (24) is movably connected to a second threaded guide (52) and moves with respect to the second container (22) by rotation of the second threaded guide (52).

The second moving element (24) is connected to the second threaded guide (52) via a second connecting element (245) which is guided by the first threaded guide (51). The second connecting element (245) has a second groove (246) formed therein. A second guard portion (70) is fit to the second groove (246). The second connecting element (245) are guided along a second slot (71) of the second guard portion (70).

The first threaded guide (51) and the second threaded guide (52) are connected to the gears of the power transmission unit and are rotated by the gears. The thread directions of the first threaded guide (51) and the second threaded guide (52) are formed such that the first and second moving elements (14, 24) move in the same direction when a ring gear (41) of the power transmission unit (40) is rotated.

The first liquid can be a cell culture fluid and the second liquid can be hydrogel. The second container (22) is illustrated as being bigger than the first container (12) in the accompanying drawings. It is just because the amount of the hydrogel is generally more that that of cell culture fluid. The size of the container and the kind of liquid in the container can be determined according to needs.

The mixing container (30) receives the first liquid and the second liquid through a first opening (34; see FIG. 3) and a second opening (36; see FIG. 3) from the first syringe (10) and the second syringe (20), respectively. The mixing container (30) comprises a mixing unit. The mixing unit comprises a first mixing portion (322) including wing (321) which radially extends from a shaft (325) and a second mixing portion (324) including a spiral portion (323) formed along the up and down directions of the shaft. The spiral portion (323) can extend along the longitudinal direction of the shaft (325). The shaft (325) is connected to a rod (53) as shown in FIG. 2. The rod (53) is rotated by the rotation of a sun gear (42) of the power transmission unit (40). When the rod (53) is rotated, the shaft (325) which is connected to the rod is rotated to mix the material in the mixing container (30).

It is preferred that the mixing container is formed so as to become narrower toward a nozzle (35) for efficient mixing.

Figure 4:
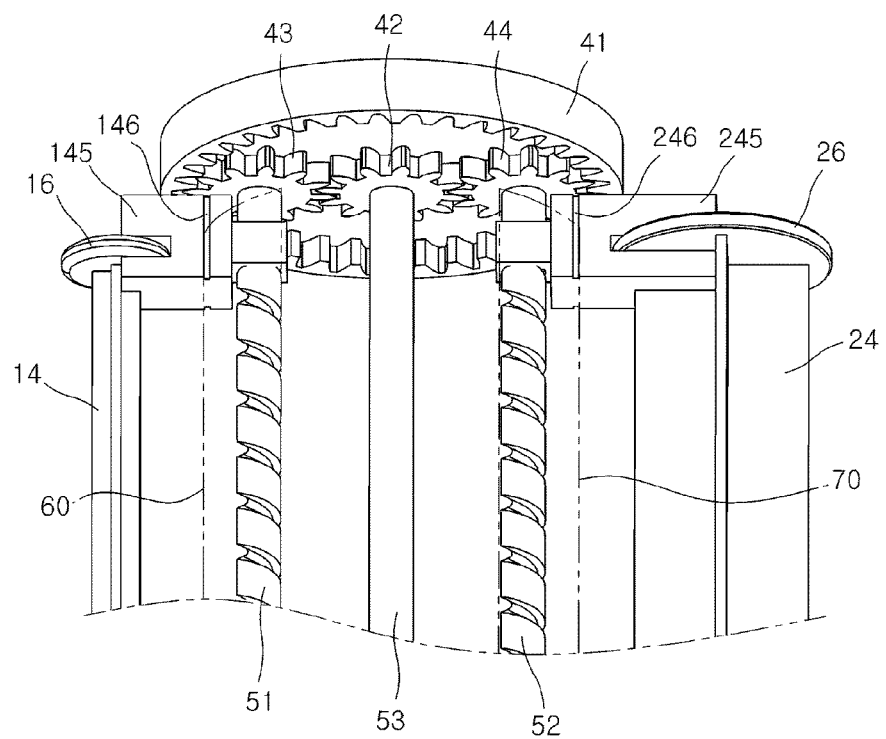
FIG. 4 is a partial perspective view of the upper portion of the device shown in FIG. 1.
Figure 5:
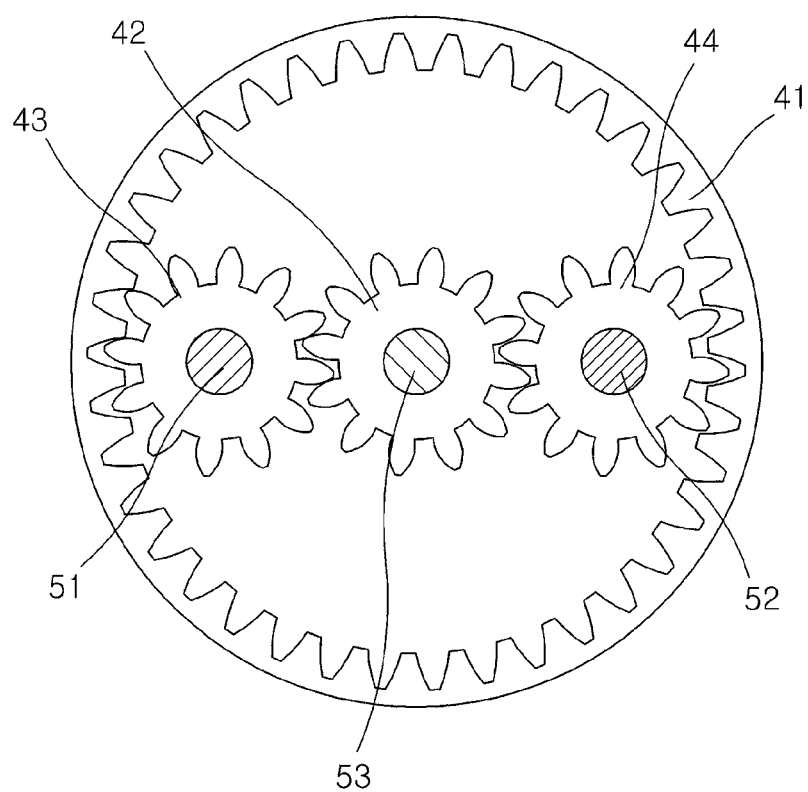
FIG. 5 is a bottom view of the power transmission unit of the device shown in FIG. 1.

FIGS. 4 and 5 show a detailed structure of the power transmission unit (40).

The power transmission unit (40) can include a ring gear (41), a sun gear (42), a first planetary gear (43) and a second planetary gear (44).

The sun gear (42) is connected to the rod (53) so as to rotate the rod; the first planetary gear (43) is connected to the first threaded guide (51) so as to rotate the first threaded guide; and the second planetary gear (44) is connected to the second threaded guide (52) so as to rotate the second threaded guide. The first planetary gear (43) and the second planetary gear (44) engage with the sun gear (42). The sun gear (42) is provided to rotate by rotation of the ring gear (41).

Figure 3:
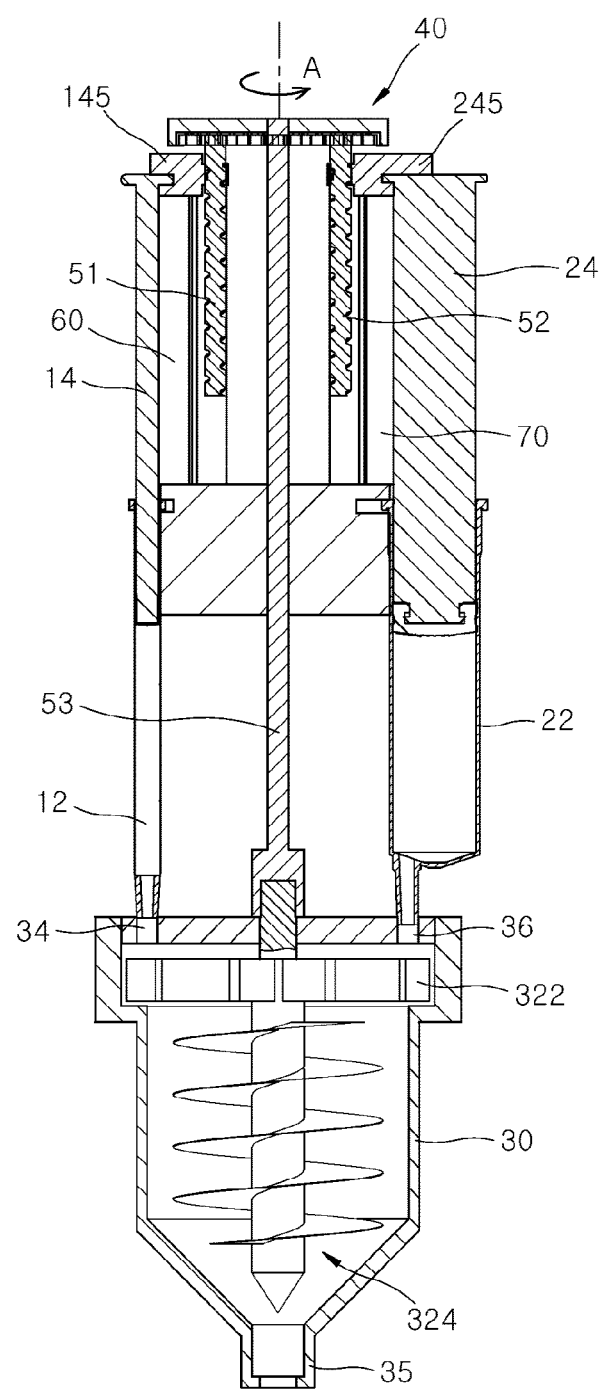
FIG. 3 is a cross sectional view of the device shown in FIG. 1.

Hereinafter, the operation of the mixing device of the present disclosure will be described with reference to FIG. 3.

The mixing device of the present disclosure is operated just by rotation of the ring gear (41) of the power transmission unit (40). The first threaded guide (51) and the second threaded guide (52) are rotated by the first planetary gear (43) and the second planetary gear (44). When the ring gear (41) is rotated such that the first moving element (14) and the second moving element (24) downwardly slide toward the mixing container (30), the first liquid contained in the first container (12) and the second liquid contained in the second container (22) enter the mixing container (30) through the first opening (34) and the second opening (36), respectively. The rotation of the ring gear (41) causes the rotation of the sun gear (42), thereby rotating the rod (53) and the shaft (325) of the mixing container (30). When the shaft (325) is rotated, the wing (321) and the spiral portion (323) is also rotated, thereby smoothly mixing the materials which are entering the mixing container (30). After the mixing is finished, the mixed composition is discharged through the nozzle (35) by extruding force applied by the first liquid and the second liquid which are continuously supplied into the mixing container (30).

According to the mixing device of the present disclosure, just rotation of the ring gear (40) of the power transmission unit (40) supplies the first liquid and the second liquid into the mixing container and simultaneously rotates the spiral screw of the mixing container to dynamically mix the liquids. In conclusion, the problems due to static mix can be solved according to the present disclosure. Further, supplying and mixing material can be performed without an additional power device for mixing.

While the present disclosure has been described with reference to the accompanying drawings, it should be appreciated that the scope of the present disclosure is determined by the appended claims and that the scope is not limited to the embodiments and/or the drawings. It is to be appreciated that a person skilled in the art can change or modify the embodiments without departing from the scope and spirit of the present disclosure.

The present disclosure was supported by Institute for Information & communications Technology Promotion (IITP) grant funded by the Korea government (MSIT) (NO. 20170019820012002, Development of 3D printing based artificial skin model for replacement of animal test and its commercialization).

The invention claimed is:

1. A mixing device of cell printing composition comprising:
    a first syringe comprising a first container for containing first liquid, and a first moving element discharging the first liquid contained in the first container;
    a second syringe comprising a second container for containing second liquid, and a second moving element discharging the second liquid contained in the second container;
    a mixing container comprising a rotating mixing unit, the mixing container receiving the discharged first liquid and the discharged second liquid;
    a power transmission unit for driving the first moving element, the second moving element and the mixing unit;
    a first threaded guide where the first moving element is movably connected;
    a second threaded guide where the second moving element is movably connected; and
    a rod for rotating the mixing unit;
    wherein the first moving element moves by rotation of the first threaded guide; the second moving element moves by rotation of the second threaded guide; and the first threaded guide, the second threaded guide, and the rod are rotated by the power transmission unit,
    wherein the power transmission unit comprises a ring gear, a sun gear which is rotatable by rotation of the ring gear, a first planetary gear which is engageable with the sun gear, and a second planetary gear which is engageable with the sun gear,
    wherein the first threaded guide is rotatable by the first planetary gear, the second threaded guide is rotatable by the second planetary gear, and the rod is rotatable by the sun gear,
    wherein the first moving element is connected to the first threaded guide via a first connecting portion which is guidable by the first threaded guide, and the second moving element is connected to the second threaded guide via a second connecting portion which is guidable by the second threaded guide, and
    wherein the mixing device further comprises a first guard portion having a first slot by which the first connecting portion is guided, and a second guard portion having a second slot by which the second connecting portion is guided.

2. The mixing device according to claim 1, wherein the mixing unit comprises a second mixing portion comprising a spiral portion extending up and down direction.

3. The mixing device according to claim 2, wherein the second mixing portion further comprises a shaft extending up and down direction; the spiral portion extends in the longitudinal direction of the shaft; and the shaft is connected to the rod and is rotatable by the rotation of the rod.

4. The mixing device according to claim 1, wherein the first moving element is slidable within the first container; and the second moving element is slidable within the second container.

5. The mixing device according to claim 1, wherein the first connecting portion comprises a first groove where the first guard is fit; and the second connecting portion comprises a second groove where the second guard is fit.

* * * * *